June 26, 1956 H. C. SWIM Plant Pat. 1,490
ROSE PLANT
Filed July 5, 1955
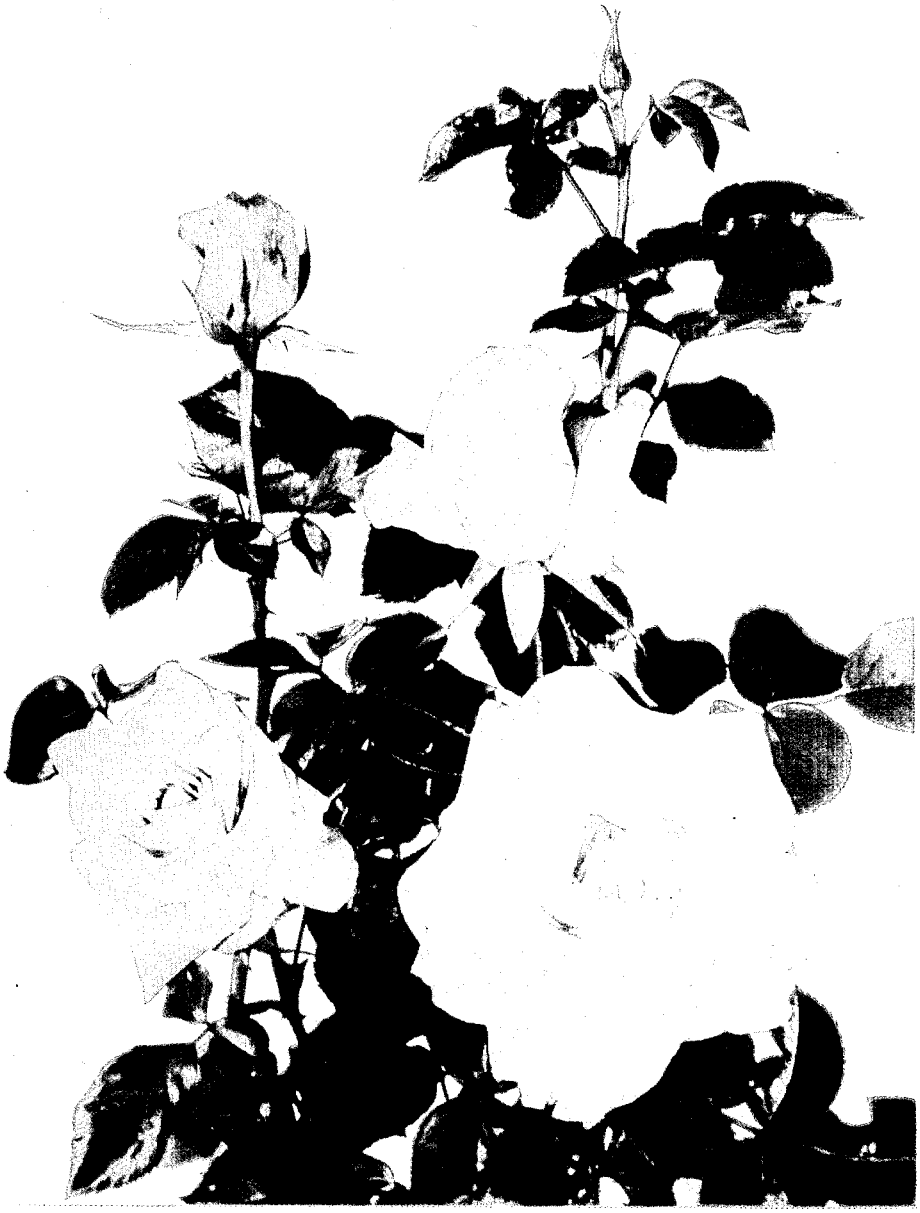
Inventor.
H. C. Swim
By: Robb & Robb
Attorneys.

United States Patent Office

Plant Pat. 1,490

Patented June 26, 1956

1,490

ROSE PLANT

Herbert C. Swim, Ontario, Calif., assignor to Armstrong Nurseries, Inc., Ontario, Calif., a corporation of California Application July 5, 1955, Serial No. 520,168

1 Claim. (Cl. 47—61)

The present invention relates to a new and distinct variety of rose plant of a class falling between the hybrid tea and hybrid polyantha classes, which was originated by me as the result of crossing the variety "Floradora" (unpatented) with the variety "First Love" (Plant Patent No. 921).

The primary objective in making this cross was to try to combine the most desirable characteristics of the two well-known parent varieties. This objective was fully achieved, as evidenced by the fact that my new variety is endowed with the following outstanding characteristics:

(1) A tall, rangy habit of growth which greatly exceeds that of either parent;

(2) A length of bud ranging from medium to long, and the somewhat urn-shaped form thereof, approaching that of the parent variety "First Love";

(3) The medium size of the blooms, approaching that of the blooms of "First Love";

(4) The habit of bearing many individual blooms on long flowering stems, as in the blooms of "First Love," while often originating from a single basic stem as in the variety "Floradora";

(5) The abundance of blooms throughout the growing season, approaching that habit of "Floradora";

(6) The good substance of the flower petals, approaching that of "Floradora," with attendant good lasting qualities of the blooms which are typical of "Floradora"; and (7) The distinctive color of the blooms, which may be generally described as a dark shade of Red, as inherited from "Floradora."

In comparison with its seed parent "Floradora," my new variety is definitely distinguished therefrom by the fact that the blooms thereof average from 3 inches to 4 inches in diameter, whereas the blooms of "Floradora" are only about 2 inches in diameter; the blooms of the new variety are double in petalage, having from about 18 to 23 petals, whereas those of "Floradora" are very double in petalage and have from about 50 to 55 petals; the blooms of the new variety are borne singly, as well as sometimes 2 or 3 to the stem, on long individual flowering stems, whereas the blooms of "Floradora" are usually borne in clusters of many flowers per cluster on relatively short individual flowering stems; the bud length of the new variety is approximately twice that of the buds of "Floradora"; the long pointed to urn shape of the buds of the new variety contrast greatly with the short pointed ovoid buds of "Floradora"; the bud and bloom color of the new variety is dark Red, whereas that of "Floradora" is popularly described as Orange-Scarlet; and the new variety is much taller and more rangy in growth than "Floradora."

As compared with its pollen parent, "First Love," the bloom color of my new variety is a dark shade of Red, whereas that of "First Love" is light Pink; the blooms of the new variety are produced in abundance, and sometimes are borne 2 or 3 flowers to the stem, whereas the blooms of "First Love" are produced less abundantly and usually with only a single flower to the stem; the foliage of the new variety is glossy, whereas that of "First Love" is non-glossy; the petal substance of the new variety is substantially heavier and thicker than that of "First Love"; the new variety has substantially less pronounced petal tips than those of "First Love"; and the new variety is substantially taller and more rangy in growth than "First Love."

The foregoing characteristics and distinctions definitely differentiate my new variety from all others of which I am aware, and asexual reproduction of the new variety by budding, as performed by me at Ontario, California, shows that said characteristics and distinctions come true to form and are established and transmitted through succeeding propagations.

The accompanying drawing shows typical specimens of the vegetative growth and flowers of my view variety in different stages of development and as depicted in color as nearly true as it is reasonably possible to make the same in a color illustration of this character.

The following is a detailed description of my new variety, with color terminology in accordance with Robert F. Wilson's Horticultural Colour Chart (hereinafter abbreviated as "Wilson") and Robert Ridgway's Color standards and Nomenclature (hereinafter abbreviated as "Ridgway"), as indicated:

Type: Bush; outdoor; seedling; for cut flowers and for garden decoration.

Class: Intermediate the hybrid tea and hybrid polyantha classes.

Breeding: Seedling.

*Seed parent.*—"Floradora."

*Pollen parent.*—"First Love."

Propagation: Holds its distinguishing characteristics through succeeding propagations by budding.

FLOWER

Locality where grown and observed: Ontario, California.

Flowers borne: Sometimes singly and sometimes 2 or 3 or more to the stem; on strong, long stems, with long individual flowering stems.

Quantity of bloom: Abundant, outdoors.

Continuity: Continuous during growing season.

Fragrance: Moderate. Nature—spicy.

Bud:

*Peduncle.*—From average length to long; average caliper; erect; usually smooth; some gland-tipped cilia. Color—between Absinthe Green, Plate XXXI (Ridgway) and Chromium Green, Plate XXXI (Ridgway), overlaid with near Neutral Red, Plate XXXVIII (Ridgway) on side exposed to the sun.

*Before calyx breaks.*—Size—medium. Form—medium length; ovoid; with foliaceous appendages, some tomentum, and few gland-tipped cilia on the surface of the bud; usually with slender, much-cut foliaceous parts extending beyond the tip of the bud equal to ¼ or more of its length.

*As calyx breaks.* — Color — between Currant Red, Plate 821/2, page 167 (Wilson) and Cardinal Red, Plate 822/1, page 168 (Wilson).

*Sepals.*—Inner surface with fine, woolly tomentum; margins of alternate sepals lined with fine, woolly tomentum; others lined with gland-tipped cilia.

*As first petal opens.*—Size—average. Form—from medium length to long; somewhat urn-shaped. Color: Outside—between Cherry, Plate 722/2, page 157 (Wilson) and Rose Red, Plate 724/1, page 158 (Wilson); inside—near Cherry, Plate 722/2, page 157 (Wilson), shading into near Cherry, Plate 722, page 157 (Wilson) toward base of petal.

*Opening.*—Opens up well; is not retarded from opening by cold, hot, wet or dry weather.

Bloom:

*Size (when fully open).*—Average; from 3 inches to 4 inches.

*Petalage.*—Double; from 18 to 23 petals, plus 3 to 7 petaloids; arranged regularly.

*Form.*—High-centered at first, but later becoming open to cupped; petals at first being cupped, with lateral margins of outer petals reflexed sometimes ½ to ¾ of petal length, and lateral margins of inner petals reflexed slightly ⅛ to ¼ of petal length, with apex of outer petals sometimes reflexed ¼ or less of petal length; becoming flat-cupped later at maturity, with lateral margins usually reflexed ½ to ¾ of petal length, and apex sometimes reflexed ¼ or more of petal length.

Petals:

*Texture.*—Thick; leathery; with inside velvety and outside satiny.

*Shape.*—Outside—broadly obovate, with apex flat; sometimes with 1 or 2 notches. Intermediate—obovate, with apex from rounded to flat; sometimes with 1 or 2 notches. Inside—narrowly obovate and somewhat irregular, with apex rounded; with 1 or 2 notches.

This description of a newly opened flower was made from a rose grown outdoors in the month of November, at Ontario, California.

*Color.*—Outside petal: Outside surface — between Cherry, Plate 722/1, page 157 (Wilson) and Rose Red, Plate 724/1, page 158 (Wilson), with small area at base of petal near attachment near Primrose Yellow, Plate 601/3, page 65 (Wilson). Inside surface—between Cherry, Plate 722, page 157 (Wilson) and Rose Red, Plate 724, page 158 (Wilson), with small area at base of petal near attachment near Primrose Yellow, Plate 601/3, page 65 (Wilson). Intermediate petal: Outside surface—between Cherry, Plate 722/2, page 157 (Wilson) and Rose Red, Plate 724/1, page 158 (Wilson), with small area at base of petal near attachment near Primrose Yellow, Plate 601/3, page 65 (Wilson). Inside surface—near Cherry, Plate 722/1, page 157 (Wilson), shading into near Cherry, Plate 722, page 157 (Wilson) with small area at base of petal near attachment near Primrose Yellow, Plate 601/3, page 65 (Wilson). Inner petal: Outside surface—near Cherry, Plate 722/2, page 157 (Wilson), with small area at base of petal near attachment near Primrose Yellow, Plate 601/3, page 65 (Wilson). Inside surface—near Cherry, Plate 722/1, page 157 (Wilson), shading into near Cherry, Plate 722, page 157 (Wilson), with small area at base of petal near attachment near Primrose Yellow, Plate 601/3 page 65 (Wilson).

This description was made from a rose that was open for 3 days outdoors in the month of November, at Ontario, California.

*Color.*—Outside petal: Outside surface—near Rose Red, Plate 724, page 158 (Wilson), with small area at base of petal near attachment near Primrose Yellow, Plate 601/3, page 65 (Wilson). Inside surface—between Cherry, Plate 722/2, page 157 (Wilson) and Rose Red, Plate 724/2, page 158 (Wilson), with small area at base of petal near attachment near Primrose Yellow, Plate 601/3, page 65 (Wilson). Inside petal: Outside surface—between Cherry, Plate 722/2, page 157 (Wilson) and Rose Red, Plate 724/1, page 158 (Wilson), with small area at base of petal near attachment near Primrose Yellow, Plate 601/3, page 65 (Wilson). Inside surface—near Cherry, Plate 722/3, page 157 (Wilson), with small area at base of petal near attachment near Primrose Yellow, Plate 601/3, page 65 (Wilson).

*General color effect.*—Newly opened flower—near Cherry, Plate 722/1, page 157 (Wilson), shading into near Cherry, Plate 722, page 157 (Wilson) toward base of petals. 3-days open—near Cherry, Plate 722/2, page 157 (Wilson), with portions of bloom shaded somewhat with near Rose Red, Plate 724/2, page 158 (Wilson).

*Behavior.*—Drop off cleanly; turning Brown shortly before dropping off; not particularly affected by cold, hot, wet or dry weather.

*Flower longevity.*—On bush in garden—4 or 5 days in November. Cut roses grown outdoors and kept at living-room temperatures—5 or 6 days in November.

REPRODUCTIVE ORGANS

Stamens: Many; arranged regularly about pistils.

Filaments: Medium length; from 5 to 10 mm. in length; most with anthers. Color—near Uranium Green, Plate 63/3, page 63 (Wilson), overlaid with near Carmine, Plate 21/3, page 21 (Wilson).

Anthers: From medium size to large; all open approximately at once. Color: upper side—margins between Lemon Yellow, Plate 4/2, page 4 (Wilson) and Buttercup Yellow, Plate 5/2, page 5 (Wilson); remainder between Geranium Lake, Plate 20/3, page 20 (Wilson) and Carmine, Plate 21/3, page 21 (Wilson). Under side—margins between Lemon Yellow, Plate 4/2, page 4 (Wilson) and Buttercup Yellow, Plate 5/2, page 5 (Wilson); remainder between Geranium Lake, Plate 20/3, page 20 (Wilson) and Carmine, Plate 21/3, page 21 (Wilson).

Pollen: Moderate quantity. Color—between Buttercup Yellow, Plate 5/2, page 5 (Wilson) and Indian Yellow, Plate 6/2, page 6 (Wilson).

Pistils: Average number; approximately 80 in number.

Styles: Moderately even; from short to average length; from 3 to 7 mm. in length; average caliper; bunched. Color—lower ½ of style near Uranium Green, Plate 63/3, page 63 (Wilson); upper ½ of style near Geranium Lake, Plate 20, page 20 (Wilson).

Stigma: Color—near Lemon Yellow, Plate 4/3, page 4 (Wilson).

Ovaries: Most enclosed in calyx, with some protruding from calyx.

Hips: From short to average length; globular; smooth; walls thick and fleshy. Color (mature)—between tangerine orange, Plate 9, page 9 (Wilson) and Orpiment Orange, Plate 10/1, page 10 (Wilson).

Sepals: Permanent; medium length; recurved. Color: Inside—between Courge Green, Plate XVII (Ridgway) and Biscay Green, Plate XVII (Ridgway); sometimes marked with between Corinthian Purple, Plate XXXVIII (Ridgway) and Neutral Red, Plate XXXVIII (Ridgway); masked by White woolly tomentum. Outside—between Biscay Green, Plate XVII (Ridgeway) and Bice Green, Plate XVII (Ridgway); sometimes marked with near Neutral Red, Plate XXXVIII (Ridgway).

Seeds: Average number; from 4 to 11 in number; medium size.

PLANT

Foliage:

*Leaves.*—Compound of usually 5 to 7 leaflets; normal abundance; medium size; leathery; glossy.

*Leaflets.*—Shape—ovoid, with apex acute. Base—round. Margin—simply serrate.

*Color.*—Mature: Upper surface—near Dark Dull Yellow-Green, Plate XXXII (Ridgway); under surface—near Chromium Green, Plate XXXII (Ridgway). Young: Upper surface—between Forest Green, Plate XVII (Ridgway) and Dark Dull Yellow-Green, Plate XXXII (Ridgway), overlaid with between Neutral Red, Plate XXXVIII (Ridgway) and Dark Corinthian Purple, Plate XXXVII (Ridgway); under surface—between Corinthian Purple, Plate XXXVIII (Ridgway) and Neutral Red, Plate XXXVII (Ridgway).

*Rachis (the supporting stem of the compound leaf).*—Average size. Upper side—grooved; hairy; some stipitate glands on edges. Under side—prickly; 2 or 3 prickles.

*Stipules.*—Medium length; wide; with medium length points turning out at an angle of more than 45°.

*Disease resistance.*—Average resistance to mildew as compared with other varieties grown under comparable cultural conditions at Ontario, California.

Growth:

*Habit.*—Bushy; upright; much-branched.

*Growth.*—Very vigorous.

*Canes.*—From medium caliper to heavy.

*Main stems.*—Color—near Light Elm Green, Plate XVII (Ridgway). Large prickles—From several to many; from medium length to long; almost straight; with moderately long, broad base. Color—between Mikado Brown, Plate XXIX (Ridgway) and Cinnamon, Plate XXIX (Ridgway). Small prickles—from few to several. Color—near Cinnamon, Plate XXIX (Ridgway). Hairs—none.

*Branches.*—Color—Between Biscay Green, Plate XVII (Ridgway) and Bice Green, Plate XVII (Ridgway). Large prickles—several; from medium length to long; almost straight; with moderately long, narrow base. Color—near Pinkish Cinnamon, Plate XXIX (Ridgway). Small prickles—several. Color—near Pinkish Cinnamon, Plate XXIX (Ridgway). Hairs—none.

*New shoots.*—Color—between Courge Green, Plate XVII (Ridgway) and Biscay Green, Plate XVII (Ridgway), overlaid with near Neutral Red, Plate XXXVIII (Ridgway). Large prickles—several; medium length; almost straight; with medium length, narrow base. Color—between Corinthian Purple, Plate XXXVIII (Ridgway) and Neutral Red, Plate XXXVIII (Ridgway). Small prickles—several. Color—between Corinthian Purple, Plate XXXVIII (Ridgway) and Neutral Red, Plate XXXVIII (Ridgway). Hairs—none.

I claim:

A new and distinct variety of rose plant of a class falling intermediate the hybrid tea and hybrid polyantha classes, substantially as herein shown and described, characterized particularly as to novelty by its tall and rangy habit of growth, the relatively long and somewhat urn-shaped form of its buds, the medium size of its blooms, the many individual blooms borne on long flowering stems which often originate from a single basic stem, the abundance of its blooms throughout the growing season, the good petal substance and attendant lasting qualities of its blooms, and the distinctive dark red general color tonality of its blooms.

No references cited.